United States Patent
Lucente-Schultz et al.

(10) Patent No.: US 9,765,254 B2
(45) Date of Patent: Sep. 19, 2017

(54) CATIONIC AMMONIUM SURFACTANTS AS LOW DOSAGE HYDRATE INHIBITORS

(71) Applicant: ECOLAB USA INC., St. Paul, MN (US)

(72) Inventors: Rebecca Michele Lucente-Schultz, Missouri City, TX (US); Jeff Servesko, Sugar Land, TX (US)

(73) Assignee: Ecolab USA Inc., St. Paul, MN (US)

(*) Notice: Subject to any disclaimer, the term of this patent is extended or adjusted under 35 U.S.C. 154(b) by 0 days.

(21) Appl. No.: 14/528,877

(22) Filed: Oct. 30, 2014

(65) Prior Publication Data

US 2016/0122619 A1 May 5, 2016

(51) Int. Cl.
*C09K 8/52* (2006.01)

(52) U.S. Cl.
CPC .......... *C09K 8/52* (2013.01); *C09K 2208/22* (2013.01)

(58) Field of Classification Search
CPC .. C09K 2208/22; C09K 8/52; C09K 2208/32; C09K 8/38; C09K 3/18; C09K 8/80; C09K 15/30; C09K 2208/08; C09K 2208/26; C09K 2208/28; C09K 2208/34; C09K 5/20; C09K 8/035; C09K 8/524; C09K 8/528; C09K 8/62; C09K 8/68; C09K 8/805; C09K 8/845; C09K 8/86; C09K 8/905; C09K 8/92; E21B 43/267; E21B 43/0211; E21B 37/06; E21B 43/26; E21B 43/16; E21B 34/14; E21B 43/01; E21B 43/168; E21B 43/36; E21B 21/10
See application file for complete search history.

(56) References Cited

U.S. PATENT DOCUMENTS

| | | | |
|---|---|---|---|
| 4,022,606 A | 5/1977 | Conrad et al. | |
| 6,566,309 B1* | 5/2003 | Klug | C08G 65/33303 507/246 |
| 7,264,653 B2 | 9/2007 | Panchalingam et al. | |
| 7,381,689 B2 | 6/2008 | Panchalingam et al. | |
| 8,618,025 B2 | 12/2013 | Webber | |
| 2012/0161070 A1* | 6/2012 | Webber | C07C 237/06 252/182.29 |

FOREIGN PATENT DOCUMENTS

GB 2349889 * 11/2000

OTHER PUBLICATIONS

Malcolm A. Kelland et al., Studies on some alkylamide surfactant gas hydrate anti-agglomerants, Chemical Engineering Science, 61, 4290-4298, 2006.*
Malcolm A. Kelland et al., Studies on some alkylamide surfactant gas hydrate anti-agglomerants, Chemical Engineering Science, 61,4290-4298, 2006.*
Internal Search Report and Written Opinion issued for PCT/US2015/058216 dated Jan. 27, 2016, 13 pages.
Kelland, M. A., et al., "Studies on Some Alkylamide Surfactant Gas Hydrate Anti-Agglomerants," Chemical Engineering Science, 2006, pp. 4290-4298, vol. 61.

* cited by examiner

*Primary Examiner* — Kumar R Bhushan

(74) *Attorney, Agent, or Firm* — Senniger Powers LLP

(57) ABSTRACT

This disclosure relates to anti-agglomerant low dosage hydrate inhibitors that can inhibit the formation of hydrate agglomerants and/or plugs. The anti-agglomerant low dosage hydrate inhibitors may be surfactants. The hydrate inhibitors may be used for inhibiting, retarding, mitigating, reducing, controlling and/or delaying formation of hydrocarbon hydrates, agglomerants of hydrates, and/or plugs. The hydrate inhibitors may be applied to prevent, reduce, and/or mitigate plugging of conduits, pipes, transfer lines, valves, and other places or equipment where hydrocarbon hydrate solids may form. The hydrate inhibitors may be cationic ammonium surfactants having an ionizable secondary amine.

16 Claims, No Drawings

CATIONIC AMMONIUM SURFACTANTS AS LOW DOSAGE HYDRATE INHIBITORS

BACKGROUND

1. Field of the Invention

This disclosure relates generally to compositions and methods for reducing or inhibiting the growth, formation, and/or agglomeration of hydrate particles in fluids. More specifically, the disclosure relates to cationic ammonium surfactants used for reducing or inhibiting hydrate agglomeration in the production and transport of petroleum fluids, whereas a petroleum fluid is defined as a mixture of varying amounts of water/brine, crude oil/condensate, and natural gas.

2. Description of the Related Art

Since Hammerschmidt discovered in 1934 that gas hydrates could block gas pipelines, research for the prevention of hydrate formation and agglomeration has become increasingly popular. Gas hydrates can easily form during the transportation of oil and gas in pipelines when the appropriate conditions are present. Water content, low temperatures, and elevated pressure are generally required for the formation of gas hydrates. The formation of gas hydrates often results in lost oil production, pipeline damage, and safety hazards to field workers. Modern oil and gas technologies commonly operate under severe conditions during the course of oil recovery and production, such as high pumping speed, high pressure in the pipelines, extended length of pipelines, and low temperature of the oil and gas flowing through the pipelines. These conditions are particularly favorable for the formation of gas hydrates, which can be particularly hazardous for oil productions offshore or for locations with cold climates.

Gas hydrates are ice-like solids that are formed from small, nonpolar molecules and water at lower temperatures and at increased pressures. Under these conditions, the water molecules can form cage-like structures around these small nonpolar molecules (typically dissolved gases such as carbon dioxide, hydrogen sulfide, methane, ethane, propane, butane and iso-butane), creating a type of host-guest interaction also known as a clathrate or clathrate hydrate. The specific architecture of this cage structure can be one of several types (called type 1, type 2, type H), depending on the identity of the guest molecules. However, once formed, these crystalline cage structures tend to settle out from the solution and accumulate into large solid masses that can travel by oil and gas transporting pipelines, and potentially block or damage the pipelines and/or related equipment. The damage resulting from a blockage can be very costly from an equipment repair standpoint, as well as from the loss of production, and finally the resultant environmental impact.

The industry uses a number of methods to prevent these blockages, such as thermodynamic hydrate inhibitors (THI), anti-agglomerant hydrate inhibitors (AAs), and kinetic hydrate inhibitors (KHIs). The amount of chemical needed to prevent blockages varies widely depending upon the type of inhibitor employed. Thermodynamic hydrate inhibitors are substances that can reduce the temperature at which the hydrates form at a given pressure and water content, and are typically used at very high concentrations (regularly dosed as high as 50% based on water content—glycol is often used in amounts as high as 100% of the weight of the produced water). Therefore, there is a substantial cost associated with the transportation and storage of large quantities of these solvents. A more cost-effective alternative is the use of low dosage hydrate inhibitors (LDHIs), as they generally require a dose of less than about 2% to inhibit the nucleation or growth of gas hydrates. There are two general types of LDHIs, kinetic hydrate inhibitors and anti-agglomerants which are both typically used at much lower concentrations. KHIs work by delaying the growth of gas hydrate crystals. They also function as anti-nucleators. In contrast, AAs allow hydrates to form but they prevent them from agglomerating and subsequently accumulating into larger masses capable of causing plugs. The function of an AA is to keep hydrate particles dispersed as a fluid slurry within the hydrocarbon phase.

BRIEF SUMMARY

The present disclosure relates to anti-agglomerant low dosage hydrate inhibitors that can inhibit the formation of hydrate agglomerants and/or plugs. In one embodiment, a hydrate inhibitor composition is disclosed. The hydrate inhibitor composition comprises at least one component selected from the group consisting of

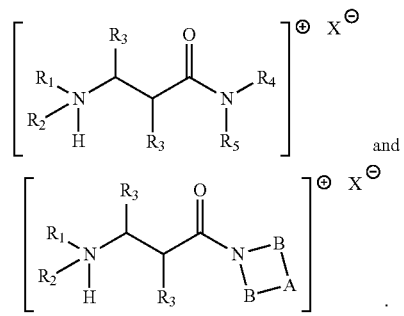

$R_1$ is an alkyl group or an alkenyl group that may contain one or more heteroatoms or ionizable heteroatoms. $R_2$ is present or not as hydrogen, depending on the ionization of the attached nitrogen atom. $R_3$ comprises a group selected from the generic formula $C_nH_{2n+1}$, wherein n is a number from 0 to 10. $R_4$ is an alkyl group or an alkenyl group that may contain one or more heteroatoms or ionizable heteroatoms. $R_5$ is selected from the group consisting of hydrogen, an alkyl group that may contain one or more heteroatoms or ionizable heteroatoms, an alkenyl group that may contain one or more heteroatoms or ionizable heteroatoms, and any combination thereof. B is a group selected from the generic formula $(CH_2)_n$, wherein n is a number from 1 to 4. A is a substituent selected from the group consisting of $CH_2$, $NR_5$, oxygen, and any combination thereof, and X is a counterion.

In another embodiment, a method of inhibiting formation of hydrate agglomerants in a fluid comprising water, a gas, and optionally liquid hydrocarbon is disclosed. The method comprises the step of adding to the fluid an effective amount of a composition comprising a hydrate inhibitor selected from the group consisting of

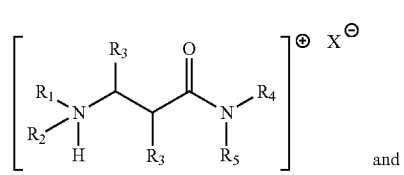

and

-continued

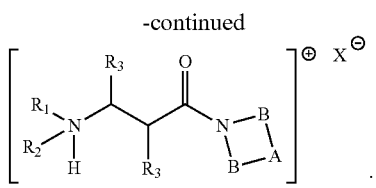

R₁ is an alkyl group or an alkenyl group that may contain one or more heteroatoms or ionizable heteroatoms. R₂ is present or not as hydrogen, depending on the ionization of the attached nitrogen atom. R₃ comprises a group selected from the generic formula $C_nH_{2n+1}$, wherein n is a number from 0 to 10. R₄ is an alkyl group or an alkenyl group that may contain one or more heteroatoms or ionizable heteroatoms. R₅ is selected from the group consisting of hydrogen, an alkyl group that may contain one or more heteroatoms or ionizable heteroatoms, an alkenyl group that may contain one or more heteroatoms or ionizable heteroatoms, and any combination thereof. B is a group selected from the generic formula $(CH_2)_n$, wherein n is a number from 1 to 4. A is a substituent selected from the group consisting of $CH_2$, $NR_5$, oxygen, and any combination thereof, and X is a counterion.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

Not applicable.

DETAILED DESCRIPTION

Various embodiments are described below. The relationship and functioning of the various elements of the embodiments may better be understood by reference to the following detailed description. However, embodiments are not limited to those explicitly disclosed in the detailed description.

The present disclosure relates to anti-agglomerant low dosage hydrate inhibitors that can inhibit the formation of hydrate agglomerants and/or plugs. In some embodiments, the anti-agglomerant low dosage hydrate inhibitors may be surfactants. Hereinafter, these compounds (anti-agglomerant low dosage hydrate inhibitors/surfactants) may be referred to as "hydrate inhibitors". Further, when referring to a hydrate inhibitor in the present disclosure, it is to be understood that the reference may refer to a hydrate inhibitor by itself, a combination of two or more hydrate inhibitors, or a composition comprising one or more of the inventive hydrate inhibitors disclosed herein. Also, when referring to a composition comprising a hydrate inhibitor, it is to be understood that the composition may comprise a single hydrate inhibitor or a combination of two or more of the presently disclosed hydrate inhibitors.

The hydrate inhibitors may be used for inhibiting, retarding, mitigating, reducing, controlling and/or delaying formation of hydrocarbon hydrates, agglomerants of hydrates, and/or plugs. In one embodiment, the hydrate inhibitors may be applied to prevent, reduce, and/or mitigate plugging of conduits, pipes, transfer lines, valves, and other places or equipment where hydrocarbon hydrate solids may form.

In some embodiments, the hydrate inhibitors are cationic ammonium surfactants. These hydrate inhibitors may be used as low dosage hydrate inhibitors for inhibiting the formation and/or agglomeration of natural gas hydrates, for example, which can lead to undesirable plugs in the petroleum industry if left untreated. In some embodiments, the hydrate inhibitors comprise an ionizable secondary amine, which is in contrast to known hydrate inhibitors, which may include tertiary, quaternary, or unionized secondary amines. In certain embodiments, the hydrate-philic group is in close proximity to the amide linkage, which is further described and depicted below. In some embodiments, the presently disclosed hydrate inhibitors are kinetic hydrate inhibitors because, in some aspects, they may act to delay hydrate formation in addition to controlling agglomeration.

The present disclosure also relates to the synthesis of such hydrate inhibitors. As mentioned above, the synthesis can be uniquely tailored so that the hydrate-philic group of the inhibitor is in close proximity to the amide linkage of the inhibitor. For example, in one embodiment, oleylamine may be reacted with methyl acrylate. The reaction product may be mixed with pyrrolidine to form an amide, which may then be treated with methanol and acetic acid, for example, to form the hydrate inhibitor.

In some embodiments, the presently disclosed hydrate inhibitors may be synthesized according to the following general procedures:

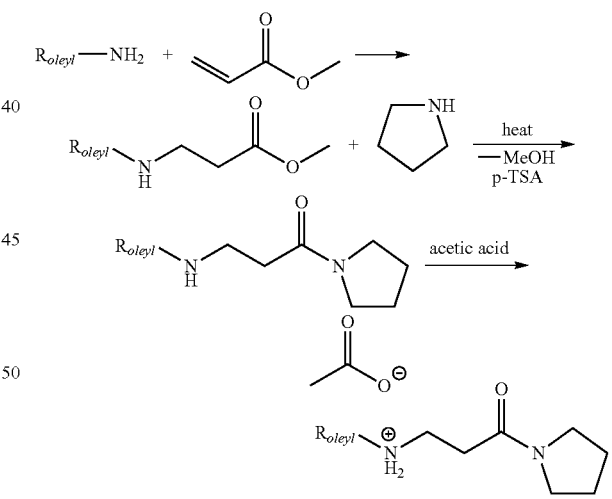

For example, the above synthesis can be carried out using the following specific reagents as illustrative examples:

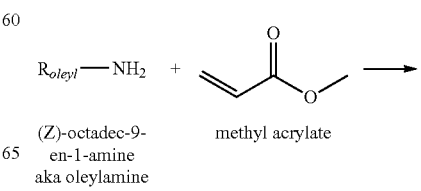

(Z)-octadec-9-en-1-amine aka oleylamine methyl acrylate

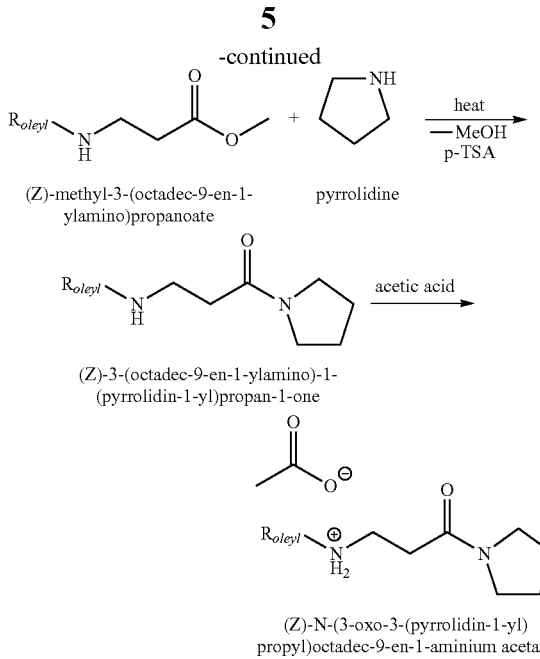

(Z)-methyl-3-(octadec-9-en-1-ylamino)propanoate + pyrrolidine (Z)-3-(octadec-9-en-1-ylamino)-1-(pyrrolidin-1-yl)propan-1-one (Z)-N-(3-oxo-3-(pyrrolidin-1-yl)propyl)octadec-9-en-1-aminium acetate In other embodiments, the presently disclosed hydrate inhibitors may be synthesized according to the following procedure:

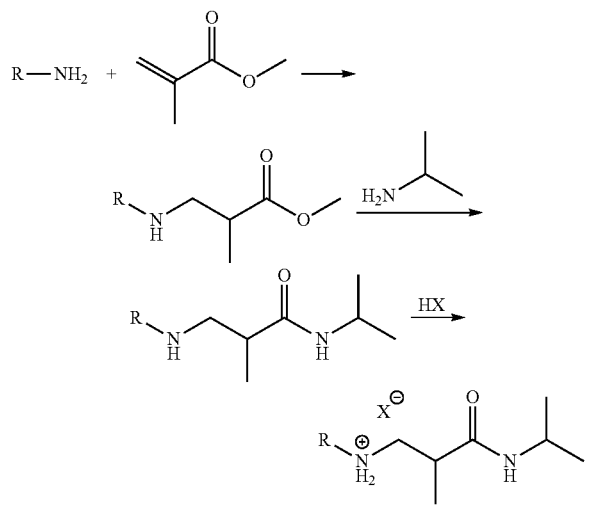

It should be noted, however, that there may be other chemical reactions that can be used to synthesize the presently disclosed hydrate inhibitors and thus, methods of making the presently disclosed hydrate inhibitors are not limited to the specific steps depicted above. All of the foregoing "R" groups are defined below in connection with the general discussion regarding the base structure of the hydrate inhibitors.

In some embodiments, the hydrate inhibitor may comprise one of the following generic chemical structures:

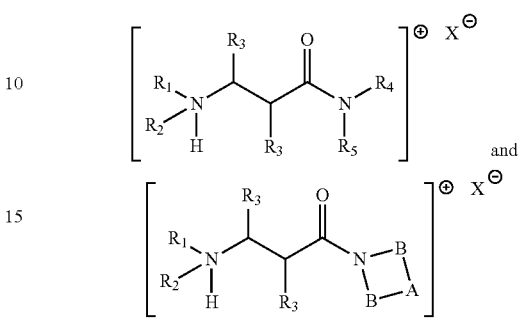

$R_1$ may be any alkyl or alkenyl group that can contain one or more heteroatoms or ionizable heteroatoms. In some embodiments, $R_1$ may comprise any group having from about 8 carbons atoms to about 20 carbon atoms, e.g. a $C_8$ to $C_{20}$ group. For example, $R_1$ may comprise a $C_8$ to $C_{12}$ group, a $C_{12}$ to $C_{16}$ group, or a $C_{16}$ to $C_{20}$ group. In some embodiments, $R_1$ comprises a $C_8$ group, a $C_{10}$ group, a $C_{18}$ group, or a $C_{20}$ group. $R_2$ may comprise hydrogen (H) or no atom or group at all, depending upon ionization of the attached nitrogen atom. $R_3$ comprises a group selected from the generic formula $C_nH_{2n,1}$, wherein "n" is a number from 0 to 10. In some embodiments, "n" is 0 or 1. $R_4$ may be any alkyl or alkenyl group that can contain one or more heteroatoms or ionizable heteroatoms and $R_5$ may be H, any alkyl group that can contain one or more heteroatoms or ionizable heteroatoms, or any alkenyl group that can contain one or more heteroatoms or ionizable heteroatoms. B comprises a group selected from the generic formula $(CH_2)_n$, wherein "n" is a number from 1 to 4. A comprises a substituent selected from $CH_2$, $NR_5$, or oxygen (O) and X may comprise any counterion, such as a halide, any carboxylate, hydrogen sulfate, dihydrogen phosphate, or nitrate. Non-limiting examples include acetate and acrylate.

In accordance with the present disclosure, the term "alkenyl" refers to a monovalent group derived from a straight, branched, or cyclic hydrocarbon containing at least one carbon-carbon double bond by the removal of a single hydrogen atom from each of two adjacent carbon atoms of an alkyl group. Representative alkenyl groups include, for example, ethenyl, propenyl, oleyl, butenyl, 1-methyl-2-buten-1-yl, and the like.

In accordance with the present disclosure, the term "alkyl" refers to a monovalent group derived by the removal of a single hydrogen atom from a straight or branched chain or cyclic saturated or unsaturated hydrocarbon. Representative alkyl groups include methyl, ethyl, propyl, butyl, pentyl, hexyl,

| Example | R1 | R2 | R4 | R5 | B1 | B2 | X |
|---|---|---|---|---|---|---|---|
| 1 | oleyl | H | — | — | C2H4 | CH2 | acetate |
| 2 | oleyl | H | — | — | C2H4 | CH2 | sulfate |
| 3 | coco | H | — | — | C2H4 | CH2 | acrylate |
| 4 | coco | H | C3H6(N(C2H4C(CH3)2)2) | H | — | — | 2 × acetate |
| 5 | coco | — | C3H6(N(C2H4C(CH3)2)2) | H | — | — | acetate |
| 6 | oleyl | H | C3H6(N(C2H4C(CH3)2)2) | H | — | — | 2 × acetate |
| 7 | oleyl | H | C3H6(N(C4H9)2)) | H | — | — | 2 × acetate |
| 8 | coco | — | C3H6(N(C4H9)2)) | H | — | — | acrylate |

-continued

| Example | R1 | R2 | R4 | R5 | B1 | B2 | X |
|---|---|---|---|---|---|---|---|
| 9 | oleyl | H | — | — | C2H4 | C3H6 | acetate |
| 10 | oleyl | H | — | — | C2H4 | C3H6 | acrylate |
| 11 | coco | H | — | — | C2H4 | C3H6 | sulfate |
| 12 | coco | H | C4H9 | C4H9 | — | — | acrylate |
| 13 | C3H6(N(C2H4C(CH3)2)2) | H | oleyl | H | — | — | 2 × acetate |
| 14 | C3H6(N(C2H4C(CH3)2)2) | — | coco | H | — | — | acrylate |
| 15 | C3H6(N(C4H9)2)) | H | oleyl | H | — | — | 2 × acetate |
| 16 | C3H6(N(C4H9)2)) | H | coco | H | — | — | 2 × acetate | heptyl, octyl, nonyl, decyl, lauryl, and the like.

Further to the generic structures depicted in the foregoing paragraph, the following are additional compositions that have been synthesized and are intended to be covered under the scope of the presently disclosed hydrate inhibitors:
Table 1:
In connection with the specific compounds listed in the foregoing Table 1 and the generic structures depicted above, $R_3$ was selected to be hydrogen and "A" was selected to be $CH_2$. Although the generic structure above only lists "B" as two of the substituents and Table 1 lists "B1" and "B2", the generic structure is intended to cover wherein the "B1" substituent is located at either of the "B" group positions and the "B2" substituent is located at either of the "B" group positions.

In some embodiments, the hydrate inhibitor comprises the following general structure:

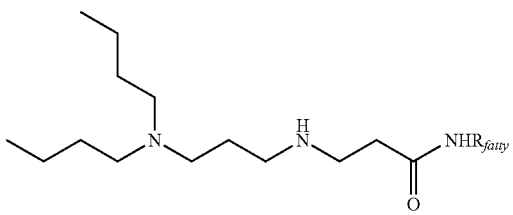

wherein "$R_{fatty}$" is any alkyl group having from about 8 carbon atoms to about 20 carbon atoms, e.g. a $C_8$ to $C_{20}$ group. For example, $R_{fatty}$ may comprise a $C_8$ to $C_{12}$ group, a $C_{12}$ to $C_{16}$ group, or a $C_{16}$ to $C_{20}$ group. In some embodiments, $R_{fatty}$ comprises a $C_8$ group, a $C_{10}$ group, a $C_{12}$ group, a $C_{18}$ group, or a $C_{20}$ group. In other embodiments, the hydrate inhibitor comprises the following general structure:

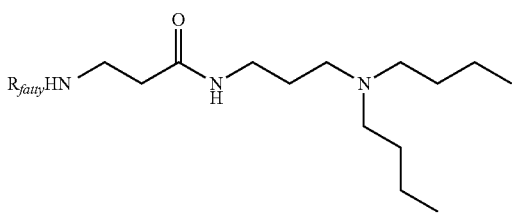

wherein "$R_{fatty}$" is any alkyl group having from about 8 carbons atoms to about 20 carbon atoms, e.g. a $C_8$ to $C_{20}$ group. For example, $R_{fatty}$ may comprise a $C_8$ to $C_{12}$ group, a $C_{12}$ to $C_{16}$ group, or a $C_{16}$ to $C_{20}$ group. In some embodiments, $R_{fatty}$ comprises a $C_8$ group, a $C_{10}$ group, a $C_{18}$ group, or a $C_{20}$ group. With respect to the term "hydrate-philic" used in the present disclosure when describing a certain portion of the hydrate inhibitor molecule, the portion of the molecule being referred to as the hydrate-philic portion is, with respect to the specific composition shown above, the portion opposite the $R_{fatty}$ group. That is, in the above example, the portion including the tertiary N atom and the two butyl groups.

In one specific embodiment, the hydrate inhibitor comprises the following general structure:

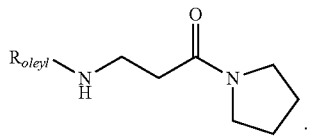

With respect to the prior art anti-agglomerant inhibitors, the hydrate-philic portion of the inhibitor molecule is also the portion of the molecule comprising the charge and the amide comprised the fatty tail, which was considered necessary for anti-agglomerant functionality. However, the present inventors have discovered a highly functional hydrate inhibitor comprising the fatty tail on the non-traditional side of the molecule (the side opposite of the amide, wherein the amide does not comprise the fatty tail) instead forming a secondary amine that can also serve as the site for salting. In the prior art, the positive charge has always centered around a quaternary or tertiary amine but not a secondary amine as in the presently disclosed hydrate inhibitors.

The compositions disclosed herein, which comprise one or more hydrate inhibitors, may further comprise one or more additional chemistries. In one embodiment, the composition further comprises at least one additional hydrate inhibitor. Exemplary additional hydrate inhibitors are disclosed in U.S. patent application Ser. No. 12/253,504, filed Oct. 17, 2008, Ser. No. 12/253,529, filed Oct. 17, 2008, Ser. No. 12/400,428, filed Mar. 9, 2009, and Ser. No. 12/967,811, filed Dec. 16, 2008, the disclosures of which are incorporated into the present application in their entireties.

In an embodiment, the composition comprising the hydrate inhibitor further comprises one or more thermodynamic hydrate inhibitors, one or more kinetic hydrate inhibitors, one or more anti-agglomerants, or any combination thereof. In some embodiments, the composition further comprises one or more asphaltene inhibitors, paraffin inhibitors, corrosion inhibitors, scale inhibitors, emulsifiers, water clarifiers, dispersants, emulsion breakers, or any combination thereof. In certain embodiments, the composition further comprises one or more polar or nonpolar solvents or a mixture thereof.

In another embodiment, the composition further comprises one or more solvents selected from the group consisting of isopropanol, methanol, ethanol, 2-ethylhexanol, heavy aromatic naphtha, toluene, ethylene glycol, ethylene glycol monobutyl ether (EGMBE), diethylene glycol monoethyl ether, xylene, or any combination thereof.

The composition comprising the hydrate inhibitor may be introduced into the fluid by any means suitable for ensuring dispersal of the hydrate inhibitor through the fluid being treated. Typically, the composition comprising the hydrate inhibitor is injected using mechanical equipment such as chemical injection pumps, piping tees, injection fittings, and the like. The composition comprising the hydrate inhibitor can be injected as prepared or formulated in one or more additional polar or non-polar solvents, depending upon the application and requirements.

Representative polar solvents suitable for formulation with the hydrate inhibitor composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide, and the like.

Representative non-polar solvents suitable for formulation with the hydrate inhibitor composition include aliphatics, such as pentane, hexane, cyclohexane, methylcyclohexane, heptane, decane, dodecane, diesel, and the like, and aromatics, such as toluene, xylene, heavy aromatic naphtha, fatty acid derivatives (acids, esters, amides), and the like.

In certain embodiments, the composition comprising the hydrate inhibitor is used in a method of inhibiting the formation of hydrate agglomerants in an aqueous medium comprising water, gas, and optionally liquid hydrocarbon. The method comprises adding to the aqueous medium an effective amount of a composition comprising one or more hydrate inhibitors.

The compositions and methods of this disclosure are effective to control gas hydrate formation and plugging during hydrocarbon production and transportation. In some embodiments, the hydrate inhibitor may be injected prior to substantial formation of hydrates. An exemplary injection point for petroleum production operations is downhole near the surface controlled sub-sea safety valve. This ensures that during a shut-in, the product is able to disperse throughout the area where hydrates will occur. Treatment can also occur at other areas in the flowline, taking into account the density of the injected fluid. If the injection point is well above the hydrate formation depth, then the hydrate inhibitor may be formulated with a solvent having a density high enough that the inhibitor will sink in the flowline to collect at the water/oil interface. Moreover, the treatment can also be used in pipelines or anywhere in the system where the potential for hydrate formation exists.

In certain embodiments, the composition comprising the hydrate inhibitor may be applied to an aqueous medium that contains various levels of salinity. In one embodiment, the fluid has a salinity of about 0% to about 25% or about 10% to about 25% weight/weight (w/w) total dissolved solids (TDS). The aqueous medium in which the disclosed compositions are applied can be contained in many different types of apparatuses, especially those that transport an aqueous medium from one location to another.

In some embodiments, the aqueous medium is contained in an oil and gas pipeline. In other embodiments, the aqueous medium is contained in refineries, such as separation vessels, dehydration units, gas lines, and pipelines. In certain embodiments, the presently disclosed hydrate inhibitors may function as corrosion inhibitors useful to inhibit the corrosion of any surface that they may contact, such as the surfaces found in refineries, such as separation vessels, dehydration units, gas lines, and pipelines. The hydrate inhibitors may also display antimicrobial properties in any of these environments.

In some embodiments, the composition comprising the hydrate inhibitor is applied to an aqueous medium that contains various levels of water cut. One of ordinary skill in the art understands that "water cut" refers to the % of water in a composition containing an oil and water mixture. In one embodiment, the water cut is from about 1% to about 80% w/w with respect to the hydrocarbon phase.

The compositions of the present disclosure may be applied to an aqueous medium using various well-known methods and they may be applied at numerous different locations throughout a given system. In one embodiment, the composition comprising the hydrate inhibitor is pumped into an oil/gas pipeline using an umbilical line. In some embodiments, capillary string injection systems may be utilized to deliver the composition. U.S. Pat. No. 7,311,144 provides a description of an apparatus and methods relating to capillary injection, the disclosure of which is incorporated into the present application in its entirety.

Various dosage amounts of the composition and/or the hydrate inhibitor(s) can be applied to the aqueous medium to inhibit the formation of hydrate agglomerants. One of ordinary skill in the art is able to calculate the amount of hydrate inhibitor or composition comprising a hydrate inhibitor for a given situation without undue experimentation. Factors that would be considered of importance in such calculations include, for example, content of aqueous medium, percentage water cut, API gravity of hydrocarbon, and test gas composition. In an exemplary embodiment, the hydrate inhibitor(s) is added in an amount from about 0.1 to about 5 volume %, based on water cut.

EXAMPLES

To evaluate the performance of the presently disclosed hydrate inhibitors and prove their superior properties as hydrate inhibitors, a rocking cell test was used. The rocking cell test is a commonly used test in the art for assessing the performance of anti-agglomerant chemistry. Briefly, chemistries are evaluated based on their ability to effectively minimize the size of hydrate agglomerant particles and then disperse those particles into the hydrocarbon phase. Chemical performance is evaluated by determining the minimum effective dose (MED) required to register as a "pass" in the rocking cell test.

The rocking cell generally includes individual cells and a rack on which the cells are placed. The cells may comprise sapphire tubing containing a stainless steel ball and can withstand pressures up to about 5,000 psi. Once the cells are mounted onto the rack, the rack rocks up and down slowly, at a rate of about 1 complete cycle (up and down) per minute. The rack is further contained within a temperature controlled bath attached to a chiller.

Anti-agglomerant test cells generally contain three components: hydrocarbon, aqueous phase, and gas. In these examples, the inventors injected a synthetic brine of about 10.3% salinity into each cell followed by a particular does of hydrate inhibitor. In the experiments the hydrate inhibitor was dosed according to the amount of aqueous phase in the test cell. The last component added to each cell was warm crude oil. The initial temperature of the test was about 80° F., and at that temperature, the cells are charged with a synthetic natural gas (SNG) mixture to about 2,500 psi. The test is a constant pressure test where the cells are left open to a booster that boosts additional gas into the cells as gas is solubilized into the fluids and/or forms hydrates. The cells were rocked for about 0.5 hours to equilibrate and mix prior to stopping at a horizontal position and cooling down to about 40° F. over an 8 hour period of time. After a shut-in time of about 48 hours at temperature, the cells were rocked again for an hour, and visual observations were recorded. Table 2 below shows the results from some of the rocking cell tests.

TABLE 2

| Example | Minimum Effective Dose Rate (vol %) |
| --- | --- |
| Comparative Example A | 5.0 |
| Comparative Example B | 3.5 |
| 1 | 2.0 |
| 2 | 1.5 |
| 16 | 1.5 |
| 4 | 1.0 |
| 8 | 0.75 |

Examples 1, 2, 16, 4, and 8 correspond to Examples 1, 2, 16, 4, and 8 in Table 1. The comparative examples were as follows:

Comparative Example A

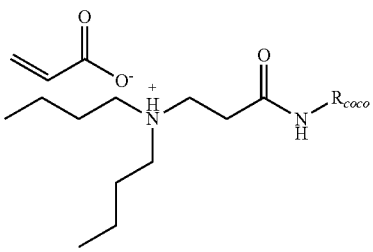

Comparative Example B

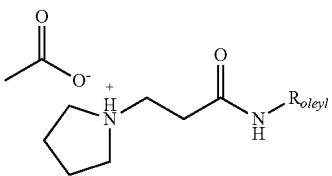

The presently disclosed hydrate inhibitors may be synthesized according to any methods known in the art. As an illustrative example, the hydrate inhibitors may be synthesized as follows:

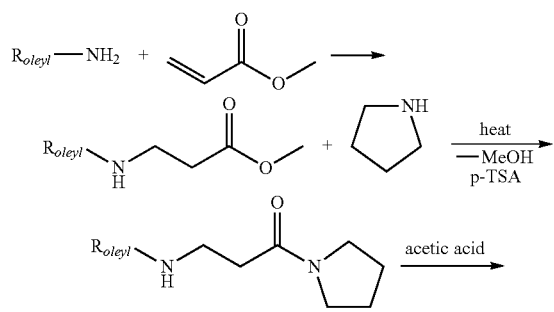

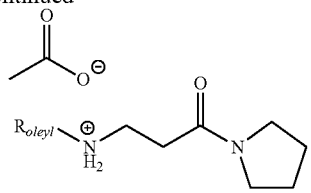

To a 500-mL, 3-neck round bottom flask was added about 100.0 g (0.374 mol) oleylamine and a magnetic stir bar. The flask was fitted with a thermocouple, reflux condenser, and addition funnel containing about 32.18 g (0.374 mol) methyl acrylate. The acrylate was added to the stirring amine slowly. Once the addition was complete, the mixture was stirred for about 1 hour. LC-MS and FT-IR confirmed full conversion of the starting materials.

To the resulting yellow liquid was added about 26.59 g (0.374 mol) pyrrolidine and catalytic para-toluenesulfonic acid (about 0.79 g). An insulated Dean-Stark apparatus was attached between the round bottom flask and reflux condenser for methanol removal. The reaction mixture was heated to about 90° C. for about 12 hours, at which time FT-IR analysis confirmed the disappearance of the ester. Upon cooling to ambient temperature, a yellow-orange liquid was formed. To the resulting amide at ambient temperature was added about 97.39 g methanol and then about 19.36 g (0.322 mol) of acetic acid, and the mixture was stirred at ambient temperature for about 2 hours to produce the hydrate inhibitor.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of inhibiting formation of hydrate agglomerants in a fluid comprising water, a gas, and optionally liquid hydrocarbon, the method comprising adding to the fluid an effective amount of a composition comprising a hydrate inhibitor selected from the group consisting of

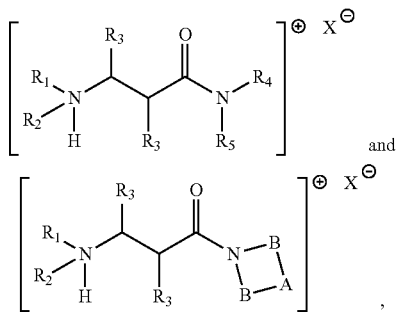

and wherein
(i) $R_1$ is an alkyl group optionally containing one or more ionizable amines or an alkenyl group optionally containing one or more ionizable amines; $R_2$ is hydrogen or absent; $R_3$ comprises a group selected from the generic formula $C_nH_{2n+1}$, wherein n is a number from 0 to 10 ; $R_4$ is an alkyl group containing one or more ionizable amines or an alkenyl group containing one or more ionizable amines; $R_5$ is hydrogen, an alkyl group optionally containing one or more ionizable amines, or an alkenyl group optionally containing one or more ionizable amines, X is a counterion; or
(ii) $R_1$ is an alkyl group containing one or more ionizable amines or an alkenyl group containing one or more ionizable amines; $R_2$ is hydrogen or absent; $R_3$ comprises a group selected from the generic formula $C_nH_{2n+1}$, wherein n is a number from 0 to 10; $R_4$ is an alkyl group optionally containing one or more ionizable amines or an alkenyl group optionally containing one or more ionizable amines; $R_5$ is hydrogen, an alkyl group optionally containing one or more ionizable amines, or an alkenyl group optionally containing one or more ionizable amines, X is a counterion; or
(iii) $R_1$ is an alkyl group optionally containing one or more ionizable amines or an alkenyl group optionally containing one or more ionizable amines; $R_2$ is hydrogen; $R_3$ comprises a group selected from the generic formula $C_nH_{2n+1}$, wherein n is a number from 0 to 10; B is a group selected from the generic formula $(CH_2)_n$, wherein n is a number from 1 to 4; A is a substituent selected from the group consisting of $CH_2$, $NR_5$, oxygen, and any combination thereof; $R_5$ is hydrogen, or an alkyl group optionally containing one or more ionizable amines; and X is a counterion.

2. The method of claim 1, wherein the effective amount is from about 0.1 to about 5 volume %, based on an amount of water.

3. The method of claim 1, wherein the fluid is contained in an oil or gas pipeline or refinery.

4. The method of claim 1, wherein the composition further comprises a thermodynamic hydrate inhibitor, a kinetic hydrate inhibitor, an anti-agglomerant, or any combination thereof.

5. The method of claim 1, wherein the composition further comprises a polar solvent, a nonpolar solvent, or a mixture thereof.

6. The method of claim 1, wherein the composition is added downhole near a surface controlled sub-sea safety valve.

7. The method of claim 1, wherein the water comprises a salinity of about 0% to about 25%, weight/weight total dissolved solids (TDS).

8. The method of claim 1, wherein X is selected from the group consisting of a halide, a carboxylate, hydrogen sulfate, dihydrogen phosphate, nitrate, and any combination thereof.

9. The method of claim 1, wherein X is acetate or acrylate.

10. The method of claim 1, wherein the hydrate inhibitor comprises a salt of the following general structure:

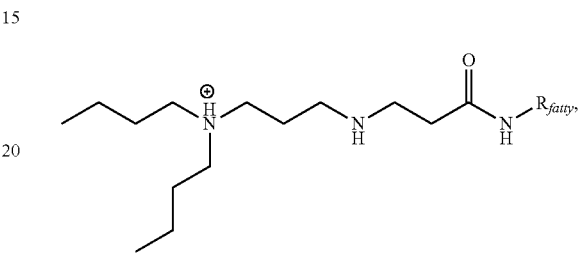

wherein $R_{fatty}$ is a $C_8$ to $C_{20}$ alkyl or alkenyl group.

11. The method of claim 1, wherein the hydrate inhibitor comprises a salt of the following general structure:

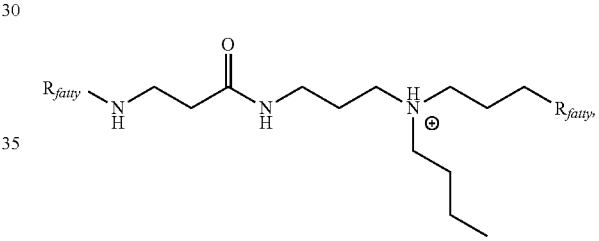

wherein $R_{fatty}$ is a $C_8$ to $C_{20}$ alkyl or alkenyl group.

12. The method of claim 1, wherein the hydrate inhibitor comprises a salt of the following general structure:

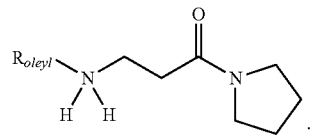

13. The method of claim 1, wherein $R_1$ is a $C_8$ to $C_{20}$ alkyl group containing one or more ionizable amines or $C_8$ to $C_{20}$ alkenyl group containing one or more ionizable amines.

14. The method of claim 13, wherein $R_3$ comprises a group selected from the generic formula $C_nH_{2n+1}$ and n is 0 or 1.

15. The method of claim 14, wherein X is selected from the group consisting of a halide, a carboxylate, hydrogen sulfate, dihydrogen phosphate, nitrate, and any combination thereof.

16. The method of claim 1, wherein $R_4$ is a $C_8$ to $C_{20}$ alkyl group containing one or more ionizable amines or a $C_8$ to $C_{20}$ alkenyl group containing one or more ionizable amines.

* * * * *

UNITED STATES PATENT AND TRADEMARK OFFICE
CERTIFICATE OF CORRECTION

PATENT NO. : 9,765,254 B2  
APPLICATION NO. : 14/528877  
DATED : September 19, 2017  
INVENTOR(S) : Rebecca M. Lucente-Schultz and Jeff Servesko Page 1 of 1

It is certified that error appears in the above-identified patent and that said Letters Patent is hereby corrected as shown below:

In the Claims

On Column 14, Claim 12, Line 47:

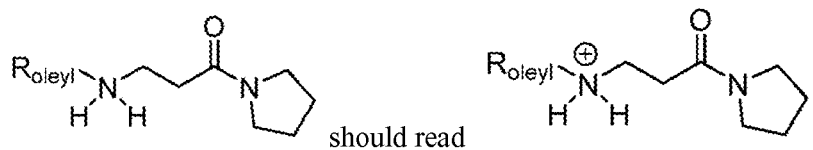 should read

Signed and Sealed this  
Second Day of January, 2018

Joseph Matal  
*Performing the Functions and Duties of the*  
*Under Secretary of Commerce for Intellectual Property and*  
*Director of the United States Patent and Trademark Office*